United States Patent [19]

Marsoner et al.

[11] Patent Number: 5,441,701
[45] Date of Patent: Aug. 15, 1995

[54] FEEDER UNIT FOR SELECTIVELY CHARGING AN ANALYZING APPARATUS

[75] Inventors: Hermann Marsoner, Steinberg; Erich Kleinhappl, Weinitzen; Reinhard Löschnigg, Graz, all of Austria

[73] Assignee: AVL Medical Instruments AG, Schaffhausen, Switzerland

[21] Appl. No.: 330,916

[22] Filed: Jun. 1, 1994

Related U.S. Application Data

[63] Continuation of Ser. No. 41,178, Apr. 1, 1993, abandoned.

[30] Foreign Application Priority Data

Apr. 2, 1992 [AT] Austria ................... 683/92

[51] Int. Cl.6 ............................................ G01N 21/84
[52] U.S. Cl. ......................... 422/63; 422/99; 422/100; 422/103; 73/864.85
[58] Field of Search ............... 422/63.81, 82, 100, 422/103, 99; 73/864.84, 864.85

[56] References Cited

U.S. PATENT DOCUMENTS

| | | | |
|---|---|---|---|
| 3,874,850 | 4/1975 | Sorensen et al. | 422/63 |
| 4,351,798 | 9/1982 | Marsoner et al. | 422/63 |
| 4,729,876 | 3/1988 | Hennessy et al. | 422/63 |
| 4,865,811 | 9/1989 | Newton et al. | 422/82 |
| 4,912,986 | 4/1990 | Marsoner et al. | 73/864.81 |
| 4,917,864 | 4/1990 | Marsoner et al. | 422/63 |

*Primary Examiner*—James C. Housel
*Assistant Examiner*—Rachel Heather Freed
*Attorney, Agent, or Firm*—Watson, Cole, Grindle & Watson

[57] ABSTRACT

A feeder unit, which is used for selectively charging an analyzing apparatus with liquid or gaseous sample-, reference- or cleaning media, comprises a sample inlet and a feeder part hinged on the feeder unit at one end. The feeder part contains an intake passage for the cleaning medium to be entered, the sample inlet having a flexible feeder funnel cooperating with a washing element which is attached to the feeder part and can be introduced into the funnel. The feeder part is configured as a cover flap swinging around a fixed pin. The intake passage for the cleaning medium opens into the washing element and is also used for delivering liquid and gaseous reference media. The washing element is located on a support which is elastically attached to the cover flap, and fits into the flexible funnel when the cover flap is closed.

5 Claims, 3 Drawing Sheets

FEEDER UNIT FOR SELECTIVELY CHARGING AN ANALYZING APPARATUS

This application is a continuation of application Ser. No. 08/041,178, filed Apr. 1, 1993, now abandoned.

BACKGROUND OF THE INVENTION

The invention relates to a feeder unit for selectively charging an analyzing apparatus with liquid or gaseous sample-, reference- or cleaning media, comprising a sample inlet and a feeder part, which is hinged on the feeder unit at one end and has an intake passage for the cleaning medium to be entered, the sample inlet being provided with a flexible feeder funnel cooperating with a washing element which is attached to the feeder part and can be introduced into the feeder funnel.

In chemical analyses using apparatus for which the above feeder unit is designed, the sample is entered via the sample inlet into a measuring cell or a block of measuring cells, where it is brought into contact with measuring elements.

DESCRIPTION OF THE PRIOR ART

Devices of this type have been used, for instance, for carrying out blood gas analyses or electrolyte analyses with the aid of electrochemical or optochemical sensors. Examples include pH, $pCO_2$, $pO_2$ measurements, or the determination of electrolyte concentrations or substrates, such as glucose, urea, creatinine, lactate, etc., in a blood sample.

In a blood gas analyzer described in U.S. Pat. No. 3,874,850 the sample inlet is closed by a cover flap. When the cover flap is closed a cap is slipped over a small flexible tube forming the end of the inlet, leaving a small gap, such that a washing solution discharged from the inlet is permitted to flow into the waste tank via the cap and a passage connected thereto, which is running inside the cover flap. The reference media are not introduced through the sample inlet, but enter the measuring cells by means of separate feed lines.

To prevent the individual media from taking different paths between the inlet opening and the measuring cells, which would bring about different measuring conditions for calibrating media and sample media, the use of a stationary feeder unit with several feed elements has been proposed, for example, in AT-PS 391 213. The actual sample inlet is positioned on a rotatable frame, such that a sealing contact may be established between each feed element and the sample inlet after a rotatory motion of the frame. This will ensure that all media enter the measuring cells through the sample inlet along the same path.

A similar solution to the problem is proposed in AT-PS 389 589. In this case the described device for selectively charging an analyzer has a stationary sample inlet, and the provided feeder unit with its feed elements performs a translational or rotatory motion positioning one feed element at a time above the sample inlet. By means of a lifting device acting parallel to the center axis of the sample inlet the feed element is inserted into the sample inlet.

A feeder unit of the type presented in the opening paragraph of this paper is described in AT-PS 372 788, for example. A feeder part hinged on one end is provided with an intake for the supply of cleaning media, and with a washing element that may be inserted into a flexible funnel of the sample inlet after the feeder part has performed a rotating and lifting motion. During the cleaning process the washing element and the feeder funnel form an annular gap defined by the shape of the funnel; through this gap a cleaning solution may be entered via a passage located in the feeder part.

Although the above devices have proved advantageous in various respects, they are quite complex mechanically. In particular, the combined lifting/rotational motion puts high demands on the control of the automatized feeding operations.

SUMMARY OF THE INVENTION

It is an object of the invention to propose a feeder unit whose mechanism is characterized by greater simplicity than that of the previous devices while maintaining their advantages, especially the use of the same sample path.

In the invention this is achieved by configuring the feeder part as a hinged cover flap turning around a fixed pin, and by proposing that the intake passage for the cleaning medium also be used for supplying liquid and gaseous reference media and that it end in the washing element, which is located on a support that is elastically attached to the cover flap, the washing element fitting into the flexible feeder funnel when the cover flap is closed and uncovering the sample inlet for sample entry when the cover flap is open. In the device of the invention the aim of using the same path for all media is achieved by means of a simple flap mechanism, which in its open position provides the path for sample entry by dropper, capillary tube or syringe, and in its closed position provides an intake passage for the reference and washing media, without involving any complex sequence of motions. As the washing element is elastically attached to the cover flap, it will fit into the upper rim of the feeder funnel, thus permitting the feeding of reference gases without any losses.

For automatic sensing of the respective position of the cover flap (open or closed), it is proposed in a further development of the invention that the feeder unit be provided with a sensing unit, preferably a photoelectric barrier, in the area of the cover flap. This sensing unit may be connected to the control unit of the analyzer, which will eliminate the possibility of operating errors.

An enhanced variant of the invention provides that the cover flap have a preferably magnetic locking mechanism holding the flap against the feeder unit in its closed position.

As a further advantage of the invention the intake passage for the reference and cleaning media passes from the cover flap into the feeder unit in the area of the flap hinge and divides into several branches, the feeder unit being provided with control elements opening one branch line at a time for the supply of a reference or cleaning medium.

It is an advantage that the intake passage for the reference and cleaning media divides into several branches leading to the tanks for the individual media only outside of the flap-type feeder part, since in this way only a single intake tube is subject to bending stresses in the area of the hinge as the cover flap opens and closes.

BRIEF DESCRIPTION OF THE DRAWINGS

The invention will be further described with reference to the accompanying drawings, in which.

DETAILED DESCRIPTION OF THE PREFERRED EMBODIMENT

Figure 1:
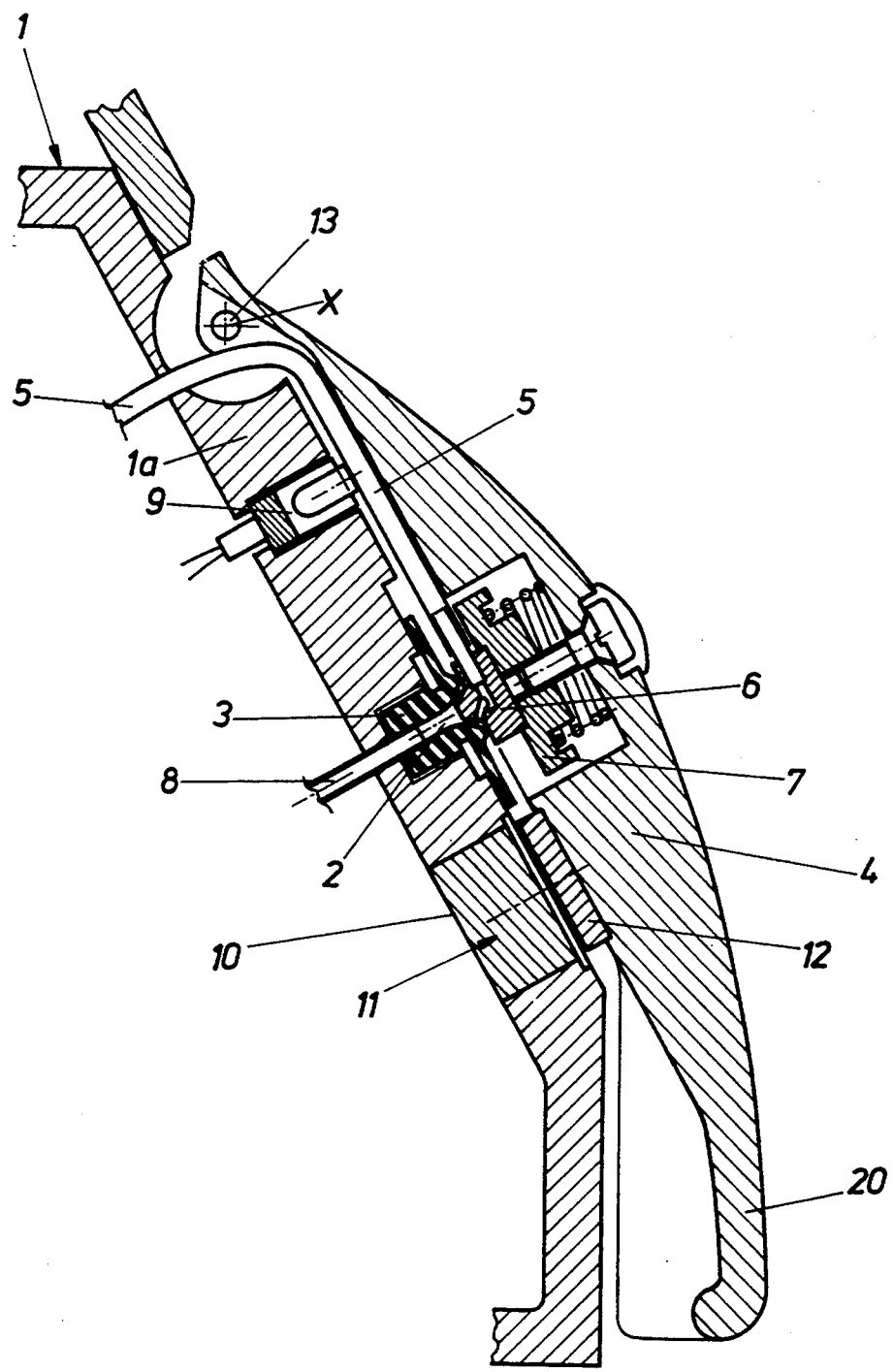
FIG. 1 shows a section of a feeder unit according to the invention.
Figure 2:
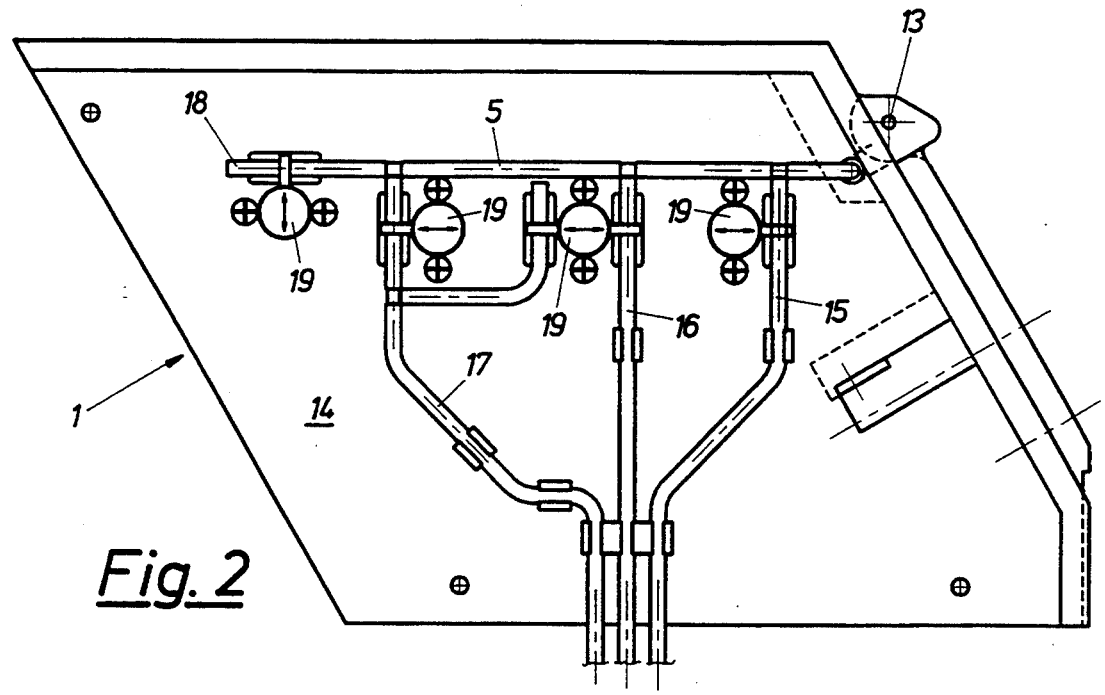
FIG. 2 is a side view of the feeder unit of FIG. 1.

FIG. 1 shows a feeder unit 1 for selectively charging an analyzing apparatus with liquid and gaseous media, which has a mounting plate 1a mounting a sample inlet 2 with a flexible feeder funnel 3. The feeder unit 1 is provided with a cover flap 4, which is hinged on one end and can be turned around a fixed pin, with an intake passage 5 for the individual reference and cleaning media, which passage 5 cooperates with the sample inlet 2, or rather, the feeder funnel 3, when the cover flap is closed. As can be appreciated from FIG. 1, the fixed pin 13 defines a pivot axis X which is perpendicular to the central flow axis of the feeder funnel 3. The intake passage 5 for the media to be entered ends in a washing element 6 which is placed on a support 7, which in turn is elastically attached to the cover flap 4. When the cover flap 4 is closed by a single rotational movement of the cover flap about the fixed hinge 13, the washing element 6 fits into the sample inlet 2, or rather, the feeder funnel 3, such that cleaning and reference media can be drawn via the intake passage 5 into the feeder funnel 3 and from there into the pre-suction passage 8. When the cover flap 4 is in its open position, the sample inlet 2 is open to sample entry by syringe or dropper.

Figure 3:
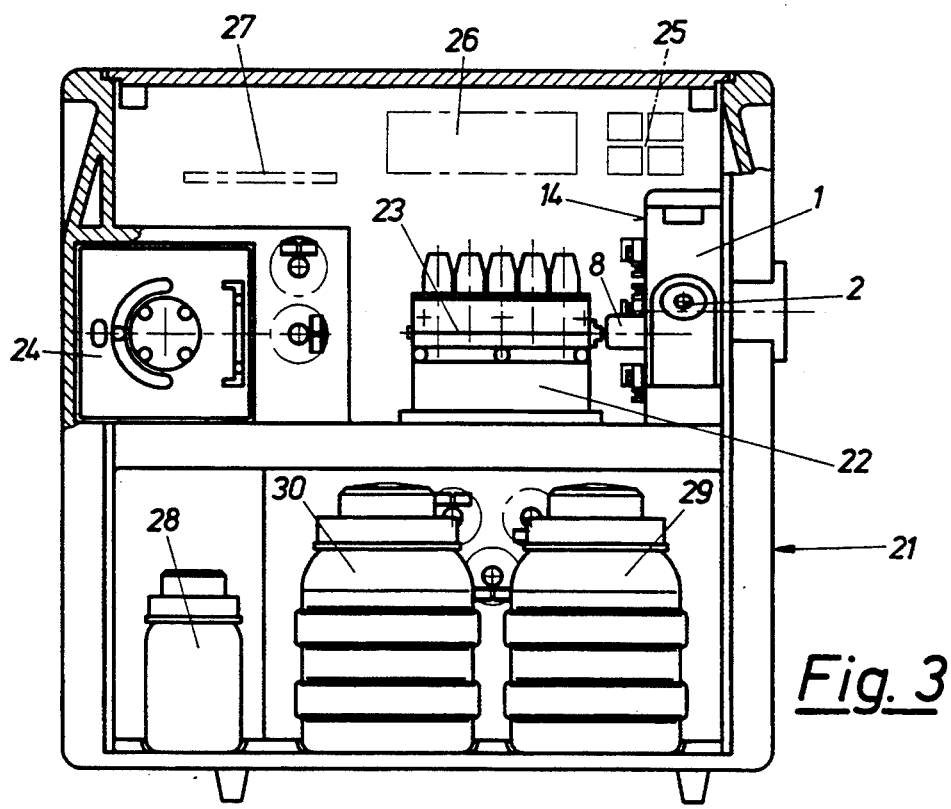
FIG. 3 shows the position of the feeder unit of FIGS. 1 and 2 in an analyzing apparatus.

In the area of the cover flap 4 the feeder unit 1 is provided with an sensing unit 9 configured as a photoelectric barrier, or a Hall sensor, or an ultrasonic source, etc., which will sense the position of the cover flap 4 and relay it to a control unit of the analyzing apparatus (FIG. 3). In addition, the device is provided with a locking mechanism 10, for example, a pot magnet 11 in the feeder unit and a ferromagnetic plate 12 in the cover flap 4, which will hold the cover flap in its closed position, a grip 20 being provided for releasing it.

In the area of the flap hinge 13 the intake passage 5 supplying the reference and cleaning media leaves the cover flap 4 to enter the feeder unit 1, at whose side face 14 it divides into several branches 15, 16, 17, 18, which are opened and closed via control elements 19, e.g., magnetic valves.

The position of the feeder unit 1 of the invention in an analyzing apparatus 21 is shown in FIG. 3. The analyzer is presented in front view, without its front part, the cover flap being removed. The pre-suction passage 8 of the feeder unit 1 is directly connected to a block of measuring cells 22, which may be moved parallel to its measuring capillary 23, decoupled from the feeder unit 1 and removed from the analyzing apparatus 21. Reference number 24 refers to a peristaltic pump handling the media, 25 to a pushbutton panel for operation of the analyzer, and 26 or 27 to an LCD display or a printer module for display of the analytical results. In the analyzing apparatus 21 exchangeable tanks 28, 29 are provided for the reference and cleaning media, as well as a waste tank 30.

Figure 4:
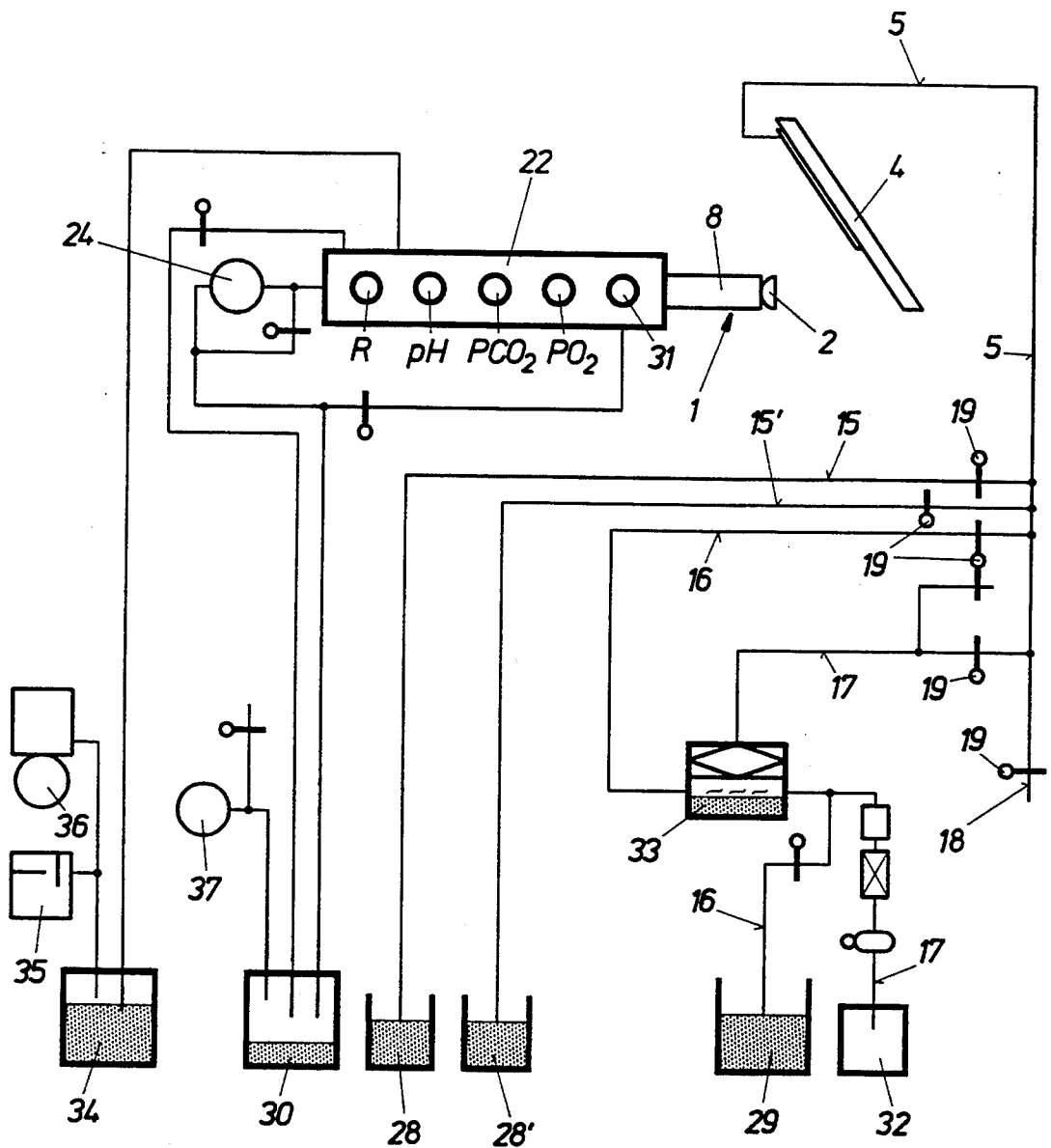
FIG. 4 shows a general diagram of the feed and drain paths of sample-, reference- and cleaning media.

FIG. 4 gives a schematical view of a block of measuring cells 22 with sensors, e.g., pH, $pCO_2$, $pO_2$ electrodes, and with a reference electrode R and a measuring cell valve 31. Via the sample inlet 2 of the feeder unit 1 and the cover flap 4 and its intake passage 5, a variety of reference and cleaning media can be admitted into the analyzing path, depending on the position of the control elements 19. For instance, reference solutions (buffer 1 and buffer 2) are delivered from tanks 28 and 28' via branch lines 15 and 15', whereas a precision gas is delivered from the gas tank 32 via branch 17. The gaseous reference medium is wetted in a gas humidifier 33 through which the cleaning liquid is passed. The washing solution is delivered to the sample inlet 2 from the tank 29 via the branch line 18 and the cover flap 4. The branch line 18 may be used to admit air. The tank 34, which is preceded by a KCl trap 35 and a pressure pump 36, contains a reference electrolyte for the reference electrode R. The waste tank 30 is connected to a vacuum pump 37.

We claim:

1. A feeder unit for delivering fluid samples to an analyzing apparatus, said feeder unit comprising a mounting means, sample inlet means mounted on said mounting means, said sample inlet means including a flexible feeder funnel which defines a central flow axis, a fixed hinge pin which defines a pivot axis which is perpendicular to said central flow axis, a cover flap which is pivotally movable about said pivot axis of said hinge pin, a support means elastically attached to said cover flap, a washing element mounted to said support means, an intake passage means connected to said washing element to supply at least one of cleaning media, liquid reference media and gaseous reference media to said washing element, said cover flap being pivotally exclusively moveable about said pivot axis of said fixed hinge pin so as to move towards said sample inlet means to a closed position wherein said washing element is located in said sample inlet means for the supply of at least one of cleaning media, liquid reference media and gaseous reference media to said sample inlet means, or away from said sample inlet means to an open position whereby said sample inlet means is uncovered and fluid samples can be supplied thereto.

2. A feeder unit according to claim 1, further comprising a sensing unit in order to sense whether the cover flap is in said open or closed position.

3. A feeder unit according to claim 2, wherein said sensing unit comprises a photoelectric barrier.

4. A feeder unit according to claim 1, wherein said cover flap is provided with a magnetic locking mechanism holding said cover flap against said mounting means.

5. A feeder unit according to claim 1, wherein said intake passage means extends from said cover flap into said mounting means adjacent said fixed hinge pin, and wherein said intake passage means is divided into several branch lines, said feeder unit further comprising control elements opening and closing said branch lines.

* * * * *